United States Patent [19]

Harris et al.

[11] 4,268,694

[45] May 19, 1981

[54] PROCESS FOR PREPARING PYROGALLOL

[75] Inventors: John F. Harris, Meldreth, Nr. Royston; Barrie J. Magill, Cambridge, both of England

[73] Assignee: Fisons Limited, Great Britain

[21] Appl. No.: 30,610

[22] Filed: Apr. 6, 1979

Related U.S. Application Data

[63] Continuation of Ser. No. 901,836, May 1, 1978, which is a continuation-in-part of Ser. No. 745,923, Nov. 29, 1976, abandoned.

[30] Foreign Application Priority Data

Nov. 29, 1975 [GB] United Kingdom ............... 49142/75
Jul. 31, 1976 [GB] United Kingdom ............... 32007/76
May 11, 1977 [GB] United Kingdom ............... 19686/77

[51] Int. Cl.³ .................... C07C 37/06; C07C 37/00
[52] U.S. Cl. ............................................... 568/763
[58] Field of Search ............................. 568/763, 772

[56] References Cited

U.S. PATENT DOCUMENTS

| | | | |
|---|---|---|---|
| 2,674,572 | 4/1954 | Gundel | 260/586 |
| 3,035,099 | 5/1962 | Lynch | 568/763 |
| 3,894,087 | 7/1975 | Gilbert | 260/586 |
| 3,904,695 | 9/1975 | Hendrich et al. | 568/770 |
| 3,957,887 | 5/1976 | Ichikawa | 568/763 |

*Primary Examiner*—Werren B. Lone
*Attorney, Agent, or Firm*—Wenderoth, Lind & Ponack

[57] ABSTRACT

A pyrogallol compound of formula

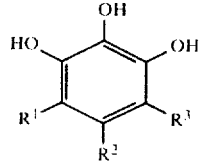

I wherein $R^1$, $R^2$ and $R^3$ each represent hydrogen or alkyl of 1-6 carbon atoms, or a salt thereof, is prepared by hydrolyzing the corresponding 2,2,6,6-tetrachlorocyclohexanone or 2,2,6,6-tetrabromocyclohexanone.

22 Claims, No Drawings

PROCESS FOR PREPARING PYROGALLOL

This is a continuation of application Ser. No. 901,836, filed May 1, 1978 which in turn is a continuation-in-part of Ser. No. 745,923, filed Nov. 29, 1976, now abandoned.

This invention relates to a process for preparing pyrogallol, 1,2,3-trihydroxybenzene, and certain derivatives thereof.

Pyrogallol or its derivatives have various uses, for instance as photographic developers, in dyeing leather and wool, in the analysis of heavy metals and as intermediates e.g. in the production of the insecticide 2,2-dimethyl-1,3-benzodioxol-4-yl methylcarbamate. At present, all the pyrogallol available in commerce is prepared by decarboxylation of gallic acid obtained from comparatively rare plane sources. This makes pyrogallol expensive and difficult to procure. Similarly pyrogallol derivatives are expensive and difficult to procure. We have now discovered a much improved process for the preparation of pyrogallol and certain derivatives thereof, which process avoids such rare plant sources and synthesises the product readily.

Accordingly, the invention provides a process for preparing a pyrogallol compound of formula

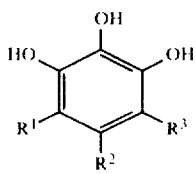

wherein $R^1$, $R^2$ and $R^3$ are the same or different and each represents a hydrogen atom or an alkyl group of 1-6 carbon atoms, or a salt thereof, which process comprises hydrolysing a 2,2,6,6-tetrahalocyclohexanone compound of formula

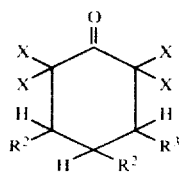

wherein each X is the same and represents a chlorine or bromine atom; and $R^1$, $R^2$ and $R^3$ are as defined above.

The process enables the pyrogallol compound or salt thereof to be synthesised in very high yields and in a high state of purity.

The pyrogallol compound forms salts by reason of its phenolic OH groups. The pyrogallol compound produced by the present invention can be in the form of its salts. The salts include particularly alkali metal, e.g. sodium or potassium especially sodium, salts and can be prepared from the pyrogallol compound itself in conventional ways, e.g. by reaction with alkali metal alkoxides. The pyrogallol compound itself can be prepared from its salts in conventional ways, e.g. by reaction with acid for example hydrochloric acid.

Usually the pyrogallol compound itself rather than a salt thereof is formed in the present hydrolysis, and the pyrogallol compound can be converted to a salt thereof if desired though this is not preferred.

Preferably X represents a chlorine atom. The alkyl group which $R^1$, $R^2$ or $R^3$ may represent may be for example methyl, ethyl or preferably t-butyl. The hydrolysis is of particular interest where at least two of $R^1$, $R^2$ and $R^3$, preferably at least $R^1$ and $R^3$, each represents a hydrogen atom. Thus, in a particular embodiment $R^1$ and $R^3$ each represent a hydrogen atom and $R^2$ represents t-butyl. Most preferred, however, is $R^1$, $R^2$ and $R^3$ each representing a hydrogen atom, so that the pyrogallol compound or salt thereof is pyrogallol itself or a salt thereof.

The hydrolysis may be considered over all:

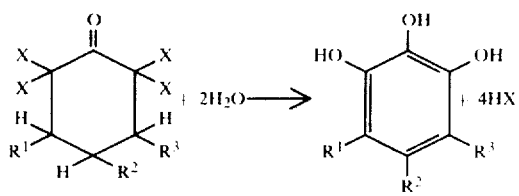

The hydrolysis can be effected directly or indirectly. Direct hydrolysis is the reaction of the tetrahalocyclohexanone compound itself with water. Indirect hydrolysis is the reaction of the tetrahalocyclohexanone compound to form a derivative which is reacted with water in a separate stage. Indirect hydrolysis can be carried out for example by reacting the tetrahalocyclohexanone compound with a metal (e.g. sodium, potassium, calcium or aluminium) alkoxide (e.g. derived from an alkanol of 1-4 carbon atoms), preferably sodium methoxide, followed by acid hydrolysis, for example by hydrochloric acid. Direct hydrolysis, however, enables the over all reaction to be conducted in a smaller number of stages, and is preferred.

The yield in the direct hydrolysis can be improved dramatically by employing a catalyst. We have found that a wide range of materials act as catalysts in this respect. There can be used as catalyst a base or an anion. An anion is included within some definitions of a base, but in the present specification we prefer to differentiate between them. The base can be for example morpholine, triethanolamine, cyclohexylamine, di-n-butylamine or 2-(diethylamino)ethanol or an anion exchange resin.

The catalyst is preferably, however, an anion. Suitable anions include (A) the anionic part of a cation exchange resin (e.g. a carboxylic acid cation exchange resin) in the hydrogen or salt form (e.g. the sodium, potassium, calcium or ammonium form), e.g. Amberlite IRC 50 in the hydrogen or sodium form, or, preferably, (B) an anion of another salt (called herein a simple salt to differentiate it from the ion exchange resin salt) e.g. citrate, dihydrogen citrate, hydrogen citrate, acetate, monochloroacetate, hydrogen malate, malate, hydrogen phthalate, hydrogen isophthalate, hydrogen tartrate, tartrate, oxalate ($^-$OOCCOO$^-$), o-nitrobenzoate, benzoate, lactate, propionate, glycolate, malonate ($^-$OOCCH$_2$COO$^-$), formate, salicylate (HOC$_6$H$_4$COO—), hydrogen adipate, adipate, hydrogen phosphate, dihydrogen phosphate, picolinate, furoate, dihydrogen pyrophosphate, hydrogen succinate, sulphamate, hydrogen phosphite, gluconate, borate (H$_2$BO$_3^-$) or fluoride.

The anion of a simple salt is preferably employed in the form of a simple salt rather than the acid. The anion catalyst can be in the form of a water-soluble metal, ammonium, or amine, salt or a mixture thereof. The amine salt can be that of a primary, secondary or tertiary amine. The amine can be aliphatic, aromatic or heterocyclic or an amine containing a mixture of such substituents on the amine nitrogen atom. It is generally preferred to use the sodium, potassium, ammonium or morpholine salt. The salt can be admixed as such or it can be generated in situ e.g. by reacting acid from which the salt is derived with alkali. For instance, cation exchange resin in the salt form can be generated in situ by providing the resin in the hydrogen form and having alkali present. Alternatively, the salt may be formed in situ by employing an ester, such as methyl oxalate, in the presence of an alkali.

Specific simple salts which are catalysts include trisodium citrate, mono-morpholine citrate, di-morpholine citrate, sodium dihydrogen citrate, disodium hydrogen citrate, sodium acetate, sodium chloroacetate, sodium hydrogen malate, disodium malate, sodium hydrogen phthalate, potassium hydrogen phthalate, ammonium hydrogen phthalate, sodium hydrogen isophthalate, sodium hydrogen tartrate, disodium tartrate, disodium oxalate, sodium-o-nitrobenzoate, sodium benzoate, sodium lactate, sodium propionate, sodium glycolate, disodium malonate, sodium formate, monosodium salicylate, sodium hydrogen adipate, disodium adipate, disodium hydrogen phosphate, sodium dihydrogen phosphate, sodium picolinate, sodium furoate, disodium dihydrogen pyrophosphate, sodium hydrogen succinate, sodium sulphamate, sodium hydrogen phosphite, sodium gluconate, monosodium borate, and potassium fluoride.

In the case of a salt of a polybasic acid, a mixed salt, e.g. a sodium potassium salt, can be employed.

The anion catalyst is preferably an anion of a carboxylic acid. The carboxylic acid can be an aliphatic, aromatic, heterocyclic or alicyclic carboxylic acid. The carboxylic acid can contain one or more carboxyl groups. Where there is more than one carboxyl group, one is preferably neutralised but the others may or may not be. Where there is more than one carboxyl group, a mixed salt, e.g. a sodium potassium salt, can be employed. The carboxylic acid preferably contains only carbon, hydrogen and oxygen atoms. Especially preferred for convenience, availability and high yield it results in is (a) a straight chain alkanoic acid of 1-6 carbon atoms, which alkanoic acid is optionally substituted by one or more groups selected from carboxyl and hydroxy groups, or (b) benzoic acid substituted by one or more groups selected from carboxyl and hydroxyl groups.

The $pK_a$ of the acid whose anion may be employed is usually in the range 2.0-6.5, preferably 2.8-5.7.

Particularly preferred specific salts are sodium acetate, disodium hydrogen citrate, sodium hydrogen phthalate or sodium hydrogen adipate.

A mixture of catalysts can be employed.

The direct hydrolysis occurs at a pH of at least 2. For maximum yield, the pH is preferably 2.8-6.0. The hydrolysis produces hydrohalic acid HX, which can lower the pH below these lower limits. For optimum yield it is preferred to maintain the pH above these lower limits during the hydrolysis. This can be done by employing catalyst in salt form as appropriate, e.g. as sodium salt, to raise the pH over what it would otherwise be, or by admixing alkali. The alkali can be any convenient alkali, such as alkali metal hydroxide, carbonate or bicarbonate, e.g. sodium carbonate, but preferably sodium hydroxide. Preferably the pH is maintained at 2.8-6.0 throughout the hydrolysis.

Although we are not bound by this theory, it seems that when anion is used as catalyst, the hydrolysis may be considered in terms of one catalyst anion displacing each halogen atom X on the 2,2,6,6-tetrahalocyclohexanone compound of formula II and then each catalyst anion being itself displaced by an HO⁻ ion from water, rearrangement occurring to result in the pyrogallol compound of formula I. It can be seen that this is analogous to the indirect hydrolysis mentioned above in which the tetrahalocyclohexanone compound is reacted with a metal alkoxide and the product is acid hydrolysed; there an alkoxide ion is the anion to displace each X atom, and the displacement of the alkoxide ion occurs in a separate stage.

When an anion is used as catalyst and the anion is that of a simple salt, the amount of catalyst is preferably at least 4 anions per molecule of tetrahalocyclohexanone. Better yields are generally obtained using 6-10 of the catalyst anions, than using 4 of the catalyst anions, per molecule of tetrahalocyclohexanone. Generally, no better yield is obtained using 16 of the catalyst anions than using 8 of the catalyst anions, per molecule of tetrahalocyclohexanone.

When an anion is used as catalyst and the anion is that of a cation exchange resin, the amount of catalyst is preferably at least 4 equivalents, especially 6-10 equivalents, of anion per mole of tetrahalocyclohexanone, generally no better yield being obtained using 16 rather than 8 equivalents of anion per mole of tetrahalocyclohexanone.

When a base is used as catalyst, it is thought, though we are not bound by this theory, that one equivalent of base reacts with one equivalent of hydrohalic acid produced in the hydrolysis. When a base is used as catalyst, the amount of catalyst is preferably at least 4 equivalents of base per mole of tetrahalocyclohexanone.

In an advantageous aspect, the invention provides a process for preparing a pyrogallol compound of formula I or a salt thereof, which process comprises reacting with water a 2,2,6,6-tetrahalocyclohexanone compound of formula II, in the presence of a catalyst which is an anion of a simple salt, the anion being derived from a carboxylic acid and/or salt thereof, which acid and/or salt thereof is present in the reaction mixture, in which process the total mole ratio of the carboxylic acid plus salt thereof to the tetrahalocyclohexanone compound is at least 10:1 and the carboxylic acid and/or salt thereof is incompletely neutralised. This mole ratio is generally between 10:1 and 30:1.

In this aspect, the carboxylic acid and/or salt thereof is incompletely neutralised. For instance, if catalyst is provided as a completely neutralised salt, e.g. sodium acetate, there must also be provided carboxylic acid, in this example usually acetic acid; this particular catalyst system can be obtained for example by admixing acetic acid and less than the equivalent amount of sodium hydroxide. If catalyst is provided as an incompletely neutralised salt, e.g. sodium hydrogen adipate, however, further carboxylic acid is not essential, though preferably it is still employed; this particular catalyst system can be obtained for example by admixing adipic acid and at most one equivalent of sodium hydroxide. If between one and two equivalents of sodium hydroxide are employed in this example, the catalyst is sodium hydrogen adipate plus disodium adipate, and this is not so preferred.

In this aspect, both carboxylic acid and salt of a carboxylic acid may be present in the reaction mixture. In that event, the salt of a carboxylic acid is preferably a salt of the same carboxylic acid as is present as acid itself.

In this aspect, preferably, sodium hydrogen adipate, especially in admixture with adipic acid, is in the reaction mixture. This is conveniently achieved by admixing adipic acid and less than 2 equivalents of sodium hydroxide with water and the 2,2,6,6-tetrahalocyclohexanone compound of formula II; when less than 1 equivalent of sodium hydroxide is employed, the sodium hydrogen adipate is in admixture with adipic acid. In another embodiment of this aspect, acetic acid and sodium acetate are in the reaction mixture. In a further embodiment of this aspect, sodium dihydrogen citrate and disodium hydrogen citrate are in the reaction mixture.

When the direct hydrolysis is used in the present invention, an organic liquid, e.g. methanol or ethanol, may be employed in the reaction mixture to give a system which is initially of one phase rather than two phases.

The present hydrolysis is preferably conducted in solution. At least the theoretical quantity of water to effect the hydrolysis must be employed, and when direct hydrolysis is employed, the solvent is preferably water in excess of that required for hydrolysis. When direct hydrolysis is employed, preferably the whole of any catalyst is in solution.

When the alkoxide route mentioned above is employed, the reaction with the alkoxide is generally conducted in the presence as solvent of the alkanol from which the alkoxide is derived, and the subsequent acid hydrolysis may be conducted in the presence as solvent of water in excess of that required for hydrolysis.

Preferably the hydrolysis employs 0.3 ml-1 liter of water per gram of tetrahalocyclohexanone compound.

The hydrolysis may for example be conducted at a temperature of 0°-250° C. e.g. 0°-120° C. The reaction mixture is usually heated. In a preferred embodiment, particularly when direct hydrolysis is employed, the temperature is 60°-140° C. Preferably direct hydrolysis is conducted under reflux.

The hydrolysis may be conducted under a pressure which is above, at, or below atmospheric pressure. The pressure may for instance be 0.1-15 atmospheres, conveniently atmospheric pressure.

The pyrogallol compound and its salts absorb oxygen when hot and the salts absorb oxygen even at ambient temperature. Accordingly, excessive heating of them should be avoided and it may be desirable in some instances to conduct the hydrolysis under an inert atmosphere, e.g. an atmosphere of nitrogen or carbon dioxide.

The product can be isolated and purified in conventional ways.

The starting material of formula II in the above process can be prepared in known ways or in ways known for analogous compounds. When it is 2,2,6,6-tetrachlorocyclohexanone or 2,2,6,6-tetrabromocyclohexanone, it can be prepared by chlorinating or brominating cyclohexanone. Alternatively, 2,2,6,6-tetrachlorocyclohexanone can be prepared by chlorinating cyclohexanol. 2,2,6,6-tetrachlorocyclohexanone or 2,2,6,6-tetrabromocyclohexanone can advantageously be prepared, however, by a process which is the subject of copending application Ser. No. 745,921—the invention of Brian John Needham and John Miller. Said process is a process for preparing 2,2,6,6-tetrachlorocyclohexanone or 2,2,6,6-tetrabromocyclohexanone, which comprises reacting in the liquid phase, in the case of the production of 2,2,6,6-tetrachlorocyclohexanone, chlorine, or in the case of the production of 2,2,6,6-tetrabromocyclohexanone, bromine, with a cyclohexanone compound of formula

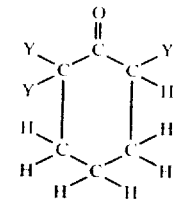

III where each Y is the same or different and represents, in the case of the production of 2,2,6,6-tetrachlorocyclohexanone, an atom of hydrogen or chlorine, and in the case of the production of 2,2,6,6-tetrabromocyclohexanone, an atom of hydrogen or bromine, in the presence of tributyl phosphine as catalyst.

The compounds of formula III employed as starting materials in the above process are either known compounds, or may be prepared by methods well known to those skilled in organic chemical synthesis for the preparation of analogous compounds.

This catalyst for the production of 2,2,6,6-tetrachlorocyclohexanone or 2,2,6,6-tetrabromocyclohexanone enables the reaction to be carried out conveniently and in high yield. The catalyst is particularly useful when the desired product is then to be hydrolysed to pyrogallol.

A catalytic amount of the catalyst must be employed. Generally, the weight of catalyst is at least 0.1%, preferably from 0.5 to 12%, of the weight of the cyclohexanone compound.

The process is of particular interest for the production of 2,2,6,6-tetrachlorocylcohexanone, so that the halogen involved is chlorine rather than bromine and Y represents an atom of hydrogen or chlorine rather than an atom of hydrogen or bromine.

The cylohexanone compound is preferably cyclohexanone itself, though an intermediately halogenated compound can be employed. For instance, to produce 2,2,6,6-tetrachlorocyclohexanone one can start from 2,2,6-trichlorocyclohexanone.

The reaction is preferably conducted in the presence of a solvent. Suitable solvents include saturated chlorinated hydrocarbons (e.g. aliphatic hydrocarbons containing 1 or 2 carbon atoms and 2-4 chlorine atoms, such as carbon tetrachloride, methylene dichloride or tetrachloroethanes), saturated hydrocarbons (e.g. those containing 5-10 carbon atoms such as pentane, hexane, cyclohexane, octane or decane) or saturated carboxylic acids (e.g. saturated aliphatic carboxylic acids containing 2-5 carbon atoms, such as acetic acid, propionic acid or butanoic acid). In the production of 2,2,6,6-tetrachlorocyclohexanone, 2,2,6-trichlorocyclohexanone may be employed as solvent. Preferably, however, the solvent is molten desired product, e.g. 2,2,6,6-tetrachlorocyclohexanone, itself. A mixture of solvents can be employed but this is not preferred.

In a preferred mode of operation, the halogen and cyclohexanone compound are fed to a reaction zone containing a solvent and the catalyst.

The reaction is usally conducted at a temperature within the range 60°-160° C., preferably 75°-110° C., e.g. 80°-110° C. The reaction temperature is preferably below the boiling point of the solvent if a solvent is employed. When molten 2,2,6,6-tetrachlorocyclohexanone is employed as solvent, the reaction temperature is its melting point as altered by the other materials present. The melting point of pure 2,2,6,6-tetrachlorocyclohexanone is 82°-83° C.

The reaction is preferably carried out under substantially anhydrous conditions, i.e. less than 1%, preferably less than 0.5%, by weight of water being present based on the weight of the cyclohexanone compound. The overall amount of chlorine or bromine employed is normally sufficient to convert all the cyclohexanone compound to desired product. When the reaction is conducted by feeding the halogen and cyclohexanone compound to a reaction zone containing a solvent and the catalyst, it is preferred, in order to minimise side reactions, that the amount of the halogen in contact with the cyclohexanone in the reaction zone be at all times at least the stoichiometric amount required to convert the cyclohexanone compound present to the desired product. For instance, starting from cyclohexanone there is preferably at least 4 moles of halogen fed per mole of cyclohexanone fed; desirably, 4–6 moles of halogen are fed while each mole of cyclohexanone is fed.

The invention is illustrated by the following Examples, in which parts and percentages are by weight.

EXAMPLE 1

A mixture of 2,2,6,6-tetrachlorocyclohexanone (100 parts) and water (532 parts) was heated to 60° C. and morpholine (149 parts) added dropwise over a period of 14 mins. The mixture was maintained at 60° C. for a further 4 mins, then cooled and filtered. The filtrate was acidified by addition of 21 parts of concentrated hydrochloric acid solution, then continuously extracted with ether. After drying over $MgSO_4$, the extract was evaporated to give 21 parts of tar, shown to contain 6 parts (11.2% yield) of pyrogallol by GLC (gas liquid chromatography) after acetylation.

EXAMPLE 2

Under a blanket of nitrogen were mixed 2,2,6,6-tetrachlorocyclohexanone (100 parts), sodium acetate (424 parts) and water (1,059 parts), and the mixture refluxed for 10 minutes. The mixture was then cooled to 50° C. when sodium bicarbonate (318 parts) was added giving severe foaming. The mixture was then extracted continuously with ether, the extract dried over magnesium sulphate and evaporated to give a residue (39 parts). The residue was triturated with chloroform (39 parts) to give after filtering and drying in air 15.2 parts of pyrogallol (28.5% yield) as a tan solid, m.pt. 130.5°-133.5° C.

EXAMPLE 3

Under a blanket of nitrogen were mixed 2,2,6,6-tetrachlorocyclohexanone (100 parts), disodium oxalate (456 parts) and water (1,064 parts), and the mixture refluxed for two hours. The mixture was then extracted continuously with ether and dried over sodium sulphate. After filtering, the extract was evaporated to give 52.2 parts of residue shown to contain pyrogallol (24.5 parts, 46% yield) by GLC after conversion to the triacetate.

Example 4

2,2,6,6-Tetrachlorocyclohexanone (2.36 g, 0.01 M) was added to 35 mls of a stirred 27% sodium methoxide solution (0.17 M) under nitrogen at 24° C. The temperature of the mixture rose and was held at 45° C. by external cooling. When the exotherm had finished, the mixture was cooled in ice and concentrated hydrochloric acid (17 mls) and water (28 mls) were added. The methanol was distilled from the reaction mixture under nitrogen, and the resultant aqueous solution was continuously extracted with ether. The ether extract was dried ($MgSO_4$) and ether removed under vacuum to give a residue (0.85 g) analysing as 18% pyrogallol. This represents a pyrogallol yield of 12.2%.

EXAMPLE 5

2,2,6,6-Tetrachlorocyclohexanone (4.72 g, 0.02 M) was added to a solution of disodium hydrogen citrate (0.16 M) made by adding with cooling sodium hydroxide (12.8 g) to a solution of citric acid monohydrate (33.6 g) in water (50 mls). The mixture was stirred and heated to reflux. The reaction mixture was sampled at intervals and analysed for free chloride until the samples showed the reaction was complete. The total reflux time was 4 hours. The reaction mixture was continuously extracted with ether. The ether extract was dried ($MgSO_4$), filtered and the ether removed to give a residue (2.74 g) analysing as 77.5% pyrogallol. The pyrogallol yield is 84.4%.

EXAMPLE 6

2,2,6,6-Tetrachlorocyclohexanone (4.72 g, 0.02 M) was added to a mixture of phthalic acid (26.5 g, 0.16 M) in water (75 mls) to which sodium hydroxide (6.4 g, 0.16 M) had been added. The mixture was heated to reflux for 1½ hours. Sodium hydroxide solution (5 mls of 5 N) was added over 5 minutes and the mixture was heated at reflux for a further 2½ hours. A sample was analysed for free chloride and this indicated the reaction was complete. Concentrated hydrochloric acid (13 mls) was added at 90° C. The reaction mixture was cooled to 5° C. and the phthalic acid was removed by filtration. The pH of the filtrate was adjusted to 3.5 and it was continuously extracted with ether. The ether extract was dried ($Na_2SO_4$), filtered and the ether removed to give crude product (3.04 g) which contained 2.02 g of pyrogallol. This represents a pyrogallol yield of 80%.

EXAMPLE 7

Glacial acetic acid (9.6 g, 0.16 M) was dissolved in distilled water and the pH was adjusted to 4.7 with 10 N sodium hydroxide solution. The volume of the solution was adjusted to 55 mls by dilution with distilled water. 2,2,6,6-Tetrachlorocyclohexanone (4.72 g, 0.02 M) was added and the mixture was heated to reflux. The pH of the reaction mixture was kept at 4.7 by the addition of 5 N sodium hydroxide solution. Samples were taken intermittently and analysed for free chloride to determine the end of reaction. The resulting aqueous solution was continuously extracted with ether. The ether extract was dried ($Na_2SO_4$), filtered and the ether removed to give crude product (3.5 g) which contained 1.46 g of pyrogallol. The pyrogallol yield was 58%.

EXAMPLE 8

Amberlite IRC 50 ion exchange resin in the sodium form (16.8 g, dry) was suspended in distilled water (50 mls). 2,2,6,6-Tetrachlorocyclohexanone (4.72 g, 0.02 M) was added and the mixture was heated to reflux for 1½ hours by which time the pH had fallen from 6.2 to 1.7. The pH was adjusted to 3.8 and reflux was continued for a further 4 hours during which the pH was kept between 2 and 4 by the addition of 5 N sodium hydroxide solution. A chloride analysis indicated 92% completion of the hydrolysis. The resin was filtered off and the reaction mixture was continuously extracted with ether. The ether extract was dried, filtered, and the ether removed to leave a brown oil (1.2 g). This analysed as 19.6% pyrogallol, representing a 9.3% pyrogallol yield.

EXAMPLE 9

2,2,6,6-Tetrachlorocyclohexanone (4.72 g, 0.02 M) was added to distilled water (50 mls) and the pH was adjusted to 5.0 with 5 N sodium hydroxide solution. The mixture was stirred and heated to reflux and the pH was kept 5.0 by the addition of sodium hydroxide solution. The mixture was sampled at intervals and analysed for free chloride until the reaction was complete. The reaction mixture was ether extracted and the ether extract was dried ($Na_2SO_4$), filtered and the ether distilled off to give a brown oil (1.3 g). This contained 0.03 g of pyrogallol which represents a 1.2% yield.

EXAMPLE 10

Following Example 9 but maintaining the pH at 3.0 gave a 3.7% yield of pyrogallol.

EXAMPLE 11

Following Example 5 but using 0.02 moles of 2,2,6,6-tetrabromocyclohexanone instead of the tetrachlorocyclohexanone gave a 44% yield of pyrogallol.

EXAMPLES 12–52

A suspension of 2,2,6,6-tetrachlorocyclohexanone (4.72 g, 0.02 M) was heated under reflux with an aqueous solution/suspension of the catalyst compound listed below (0.16 M; in the case of the Amberlite IRC 50, 16.0 g of dry resin were employed) in 50 mls of water. The mixture was sampled at intervals and analysed for free chloride to determine the end point of the reaction. The aqueous reaction mixture was then filtered if necessary and extracted continuously with ether. The ether extract was dried ($Na_2SO_4$), filtered and the ether removed to give the crude pyrogallol. This was analysed to determine the yield.

| Example | Catalyst Compound | Yield of Pyrogallol, % |
|---|---|---|
| 12 | Trisodium Citrate | 25.5 |
| 13 | Sodium Dihydrogen Citrate | 31.0 |
| 14 | Sodium Chloroacetate | 31.0 |
| 15 | Sodium Hydrogen Malate | 71.0 |
| 16 | Disodium Malate | 52.0 |
| 17 | Potassium Hydrogen Phthalate | 75.0 |
| 18 | Ammonium Hydrogen Phthalate | 52.0 |
| 19 | Sodium Hydrogen Isophthalate | 59.8 |
| 20 | Sodium Hydrogen Tartrate | 58.0 |
| 21 | Disodium Tartrate | 60.5 |
| 22 | Disodium Oxalate | 44.0 |
| 23 | Sodium o-Nitrobenzoate | 35.1 |
| 24 | Sodium Benzoate | 49.5 |
| 25 | Sodium Lactate | 68.5 |
| 26 | Sodium Propionate | 42.9 |
| 27 | Sodium Glycolate | 57.0 |
| 28 | Disodium Malonate | 27.0 |
| 29 | Sodium Formate | 20.8 |
| 30 | Sodium Salicylate | 29.0 |
| 31 | Sodium Hydrogen Adipate | 82.0 |

-continued

| Example | Catalyst Compound | Yield of Pyrogallol, % |
|---|---|---|
| 32 | Disodium Adipate | 46.0 |
| 33 | Amberlite IRC 50 H⁺ form | 17.0 |
| 34 | Disodium Hydrogen Phosphate | 22.6 |
| 35 | Sodium Dihydrogen Phosphate | 32.5 |
| 36 | Monosodium Borate | 7.0 |
| 37 | Potassium Fluoride | 16.0 |
| 38 | Ethylene Diamine Tetraacetic acid, Disodium Salt | 49.0 |
| 39 | Sodium Hydrogen Fumarate | 53 |
| 40 | Disodium Fumarate | 58 |
| 41 | Sodium Hydrogen 1,2,3,6-Tetra hydrophthalate | 62 |
| 42 | Sodium Hydrogen Maleate | 34 |
| 43 | Sodium Pivalate | 11 |
| 44 | Dipotassium Oxalate | 71 |
| 45 | Sodium Picolinate | 6 |
| 46 | Sodium Furoate | 19 |
| 47 | Disodium Di Hydrogen Pyrophosphate | 47 |
| 48 | Sodium Hydrogen succinate | 76 |
| 49 | Sodium sulphamate | 13 |
| 50 | Sodium hydrogen phosphite | 18 |
| 51 | Dimethyl oxalate | 25 |
| 52 | Sodium gluconate | 67 |

EXAMPLE 53

2,2,6,6-Tetrachlorocyclohexanone (4.72 g, 0.02 M) was added to a solution of morpholine citrate made by adding with cooling morpholine (24.6 mls 0.283 moles) to a solution of citric acid monohydrate (33.6 g, 0.16 M) in water (50 mls). The mixture was stirred and heated to reflux. The reaction mixture was sampled at intervals and analyzed for free chloride until the samples showed the reaction was complete. The total reflux time was 3 hours. The reaction mixture was continuously extracted with ether. The ether extract was dried ($MgSO_4$), filtered and the ether removed to give a residue (5.4 g) analysing as 33.6% pyrogallol. The pyrogallol yield is 71.9%.

EXAMPLE 54

2,2,6,6-Tetrachloro-4-methylcyclohexanone (5.0 g, 0.02 M) was added to a solution of sodium hydrogen phthalate (30.1 g, 0.16 M) in 50 mls of water. The mixture was heated at reflux and sampled at intervals for free chloride determination. When the reaction was complete the mixture was cooled, filtered, ether extracted and the ether removed to give a crude product, 3.8 g, which contained 1,2,3-trihydroxy-5-methylbenzene (methyl pyrogallol). (1.26 g). This represents a 45% yield.

EXAMPLE 55

45 g of 2,2,6,6-tetrachlorocyclohexanone (TCCH) and 5 g of tributyl phosphine were charged to a 500 ml flask fitted with a mechanical stirrer, a thermometer, a water condenser and a chlorine inlet tube having a sinter outlet to the bottom of the flask. The flask was heated, and the melt at 85°–90° C. was swept with nitrogen for 10 minutes. At 95°–105° C. 276 g of chlorine and 66 g of cyclohexanone were charged to the flask continuously over 6.7 hours. The mole ratio of chlorine to cyclohexanone was kept at 5.8 throughout the addition. Chlorine was then added continuously at the same rate as it was before for 1½ hours while maintaining the same temperature. 375 ml n-hexane were added to the reaction mixture, which was then heated to give a clear solution.

Cooling of the solution to 5° C. precipitated crystals of TCCH, which after filtration and drying contained 137.0 g (86.5%) of freshly formed TCCH (i.e. the TCCH over and above that charged initially to the flask). Analysis showed that the resultant TCCH was 99% pure.

EXAMPLE 56

Pure 2,2,6,6-tetrachlorocyclohexanone (TCCH, 4.72 g, 0.02 mole), sodium acetate (26.24 g, 0.32 mole), glacial acetic acid (9.6 g, 0.16 mole) and water (55 mls, 3.06 mole) were mixed and heated to 100° C. for 5 hours in a flask fitted with a stirrer, condenser, thermometer and pH electrode. During this time, the pH changed from an initial 5.03 to 4.89 and chloride determination indicated complete reaction of the chloro groups.

Extraction of the reaction product with ether, and evaporation of the ether extract gave a brown solid, 3.25 g, containing 56.7% pyrogallol, representing 1.843 g, (75.3% of the theoretical yield).

EXAMPLE 57

As Example 56 but with sodium acetate (16.4 g, 0.2 mole), acetic acid (16.8 g, 0.28 mole) and water (50 mls, 2.78 moles). The pH fell from 5.03 to 4.38, and the yield of pyrogallol was 82.5% theoretical, as 3.79 g of 55% pure product.

EXAMPLE 58

As Example 56 but with sodium acetate (13.12 g, 0.16 mole), acetic acid (9.6 g, 0.16 mole) and water (40 mls, 2.22 moles). The pH fell from 4.98 to 4.22. The yield of pyrogallol was 77.2% of theoretical, as 3.44 g of 56.2% pure product.

EXAMPLE 59

Adipic acid (70.2 g, 0.48 mole) was suspended in distilled water (100 mls), and sodium hydroxide pellets (16.0 g, 0.40 M) were added. To the solution at 96° C. was added TCCH (9.44 g, 0.04 M). The mixture was heated to reflux for 4 hours. A chloride determination then showed 96.5% completion of reaction. The reaction mixture was acidified to pH 0.7 with 25 mls of concentrated hydrochloric acid, cooled to 5° C., filtered and the filter cake washed with a small amount of distilled water. The combined washings and filtrate were adjusted to pH 4.0 with 5 N NaOH and the total aqueous material was extracted with 6×210 mls of ether. The resulting ether solutions were combined and dried (over $Na_2SO_4$), and the ether was removed under vacuum to give a crude product, 6.12 grams, which contained 4.03 grams of pyrogallol. (Yield =80%).

EXAMPLE 60

A reaction carried out as in Example 59 but with 12.8 g (0.32 M) of sodium hydroxide pellets gave a 75.6% pyrogallol yield.

EXAMPLE 61

A reaction carried out as in Example 59 but with 19.2 g (0.48 M) of sodium hydroxide pellets gave a 74.6% pyrogallol yield.

EXAMPLE 62

Citric acid (84.0 g, 0.40 moles) was added to 100 mls of water, and sodium hydroxide pellets (25.6 g, 0.64 M) were added. After the addition of the sodium hydroxide the temperature was 47° C., and TCCH (9.44 g, 0.04 M) was added. The mixture was heated to 100° C. for 6 hours and was then cooled and extracted with 6×17 mls of ether. The resulting ether solutions were combined and dried over anhydrous sodium sulphate, before filtering, and removing the ether under vacuum to give a crude product (5.45 g) containing 4.36 grams of pyrogallol. (Yield =86.5%).

We claim:

1. A process for preparing a pyrogallol compound of formula:

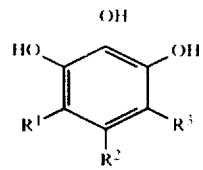

wherein $R^1$, $R^2$ and $R^3$ are the same or different and each represents a hydrogen atom or an alkyl group of 1-6 carbon atoms or a salt thereof, which process comprises the direct hydrolysis of a 2,2,6,6-tetracyclohexanone compound of formula:

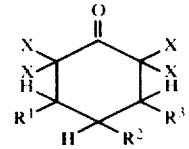

wherein each X is the same and represents a chlorine or bromine atom, and $R^1$, $R^2$ and $R^3$ are as defined above, by reacting said 2,2,6,6-tetracyclohexanone compound with water in the presence of a catalyst, said hydrolysis being conducted at a temperature of 0°-250° C. and employing 0.3 ml-1 liter of water per gram of said b 2,2,6,6-tetrahalocyclohexanone compound.

2. A process according to claim 1 wherein the pyrogallol compound is prepared.

3. A process according to claim 1 wherein X represents a chlorine atom.

4. A process according to claim 1 wherein the a catalyst is a base.

5. A process according to claim 4 wherein the base is morpholine, triethanolamine, cyclohexylamine, di-n-butylamine, 2-(diethylamino) ethanol or an anion exchange resin.

6. A process according to claim 1 wherein the catalyst is an anion.

7. A process according to claim 6 wherein the catalyst is the anionic part of a cation exchange resin in the hydrogen or salt form.

8. A process according to claim 6 wherein the catalyst is an anion of a simple salt.

9. A process according to claim 6 wherein the catalyst is an anion of a carboxylic acid.

10. A process according to claim 9 wherein the $pK_a$ of the acid is 2.8-5.7.

11. A process according to claim 8 wherein the anion is citrate, dihydrogen citrate, hydrogen citrate, acetate, monochloroacetate, hydrogen malate, malate, hydrogen phthalate, hydrogen isophthalate, hydrogen tartrate, tartrate, oxalate, o-nitrobenzoate, benzoate, lactate, propionate, glycolate, malonate, formate, salicylate, hydrogen adipate, adipate, hydrogen phosphate, dihydrogen phosphate, picolinate, furoate, dihydrogen pyrophosphate, hydrogen succinate, sulphamate, hydrogen phosphite, gluconate, borate or fluoride.

12. A process according to claim 8 wherein the anion is employed in the form of a simple salt.

13. A process according to claim 12 wherein the salt is a sodium, potassium or ammonium salt.

14. A process according to claim 8 wherein the catalyst is employed in the form of sodium acetate, disodium hydrogen citrate, sodium hydrogen phthalate or sodium hydrogen adipate.

15. A process according to claim 1 wherein the pH is maintained at 2.8–6.0 throughout the hydrolysis.

16. A process according to claim 1 wherein the hydrolysis is conducted at a temperature of 60°–140° C.

17. A process for preparing a pyrogallol compound of formula:

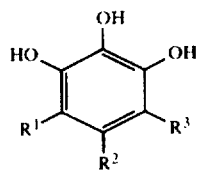

where $R^1$, $R^2$ and $R^3$ are the same or different and each represents a hydrogen atom or an alkyl group of 1–6 carbon atoms or a salt thereof, which process comprises the indirect hydrolysis of a 2,2,6,6-tetrahalocyclohexanone compound of formula:

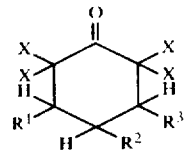

wherein each X is the same and represents a chlorine or bromine atom, and $R^1$, $R^2$ and $R^3$ are as defined above, by reacting said 2,2,6,6-tetrahalocyclohexanone compound to form a derivative which is then reacted with water in a separate stage, the hydrolysis being conducted at a temperature of 0°–250° C. and employing 0.3 ml–1, liter of water per gram of said 2,2,6,6-tetrahalocyclohexanone compound.

18. A process according to claim 17 wherein the hydrolysis is carried out by reacting the 2,2,6,6-tetrahalocyclohexanone compound with a metal alkoxide to form a derivative which is then reacted with water in the presence of acid.

19. A process according to claim 18 wherein the metal alkoxide is sodium methoxide.

20. A process according to claim 17 wherein the pyrogallol compound is prepared.

21. A process accrording to claim 17 wherein X represents a chlorine atom.

22. A process for preparing pyrogallol or a salt thereof, which process comprises reacting 2,2,6,6-tetrachlorocyclohexanone with water at a temperature of 0°–250° C. and in the presence of a catalyst, employing 0.3 ml–1 liter of water per gram of said 2,2,6,6-tetrachlorocyclohexanone.

* * * * *